(12) United States Patent
Nagato et al.

(10) Patent No.: US 7,718,807 B2
(45) Date of Patent: May 18, 2010

(54) SALT OF 1,2-DIHYDROPYRIDINE COMPOUND

(75) Inventors: Satoshi Nagato, Tokyo (JP); Kohshi Ueno, Tsukuba (JP); Hiroshi Ishihara, Tsukuba (JP); Yukiko Sugaya, Tsukuba (JP); Koichi Ito, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 12/280,403

(22) PCT Filed: Apr. 27, 2007

(86) PCT No.: PCT/JP2007/059188

§ 371 (c)(1),
(2), (4) Date: Aug. 22, 2008

(87) PCT Pub. No.: WO2007/126060

PCT Pub. Date: Nov. 8, 2007

(65) Prior Publication Data

US 2009/0054654 A1 Feb. 26, 2009

(30) Foreign Application Priority Data

Apr. 28, 2006 (JP) .............................. 2006-126574

(51) Int. Cl.
*C07D 213/64* (2006.01)
(52) U.S. Cl. .................................... 546/257
(58) Field of Classification Search ................. 546/257
See application file for complete search history.

(56) References Cited

U.S. PATENT DOCUMENTS

| 6,949,571 B2 * | 9/2005 | Nagato et al. ............... 514/334 |
| 2004/0023973 A1 | 2/2004 | Nagato |
| 2006/0100249 A1 | 5/2006 | Smith |
| 2006/0270709 A1 * | 11/2006 | Gray et al. .................. 514/332 |
| 2007/0142640 A1 | 6/2007 | Arimoto et al. |

FOREIGN PATENT DOCUMENTS

| EP | 1 300 396 A1 | 4/2003 |
| EP | 1 465 626 A1 | 10/2004 |
| EP | 1 875 912 A1 | 1/2008 |
| JP | 2005-515995 A | 6/2005 |
| WO | WO-01/96308 A1 | 12/2001 |
| WO | WO-2006/004107 A1 | 1/2006 |
| WO | WO-2006/107859 A2 | 10/2006 |
| WO | WO-2006/107860 A2 | 10/2006 |
| WO | WO-2006/109876 A1 | 10/2006 |
| WO | WO-2007/072868 A1 | 6/2007 |
| WO | WO-2007/072869 A1 | 6/2007 |

OTHER PUBLICATIONS

Vippagunta et al., "Crystalline Solid", Advanced Drug Delivery Reviews 48 (2001) 3-26.*
Guillory (in Brittain ed.), Polymorphism, etc., NY: Marcel Dekker, Inc., 1999, 1-2, 183-226.*

* cited by examiner

*Primary Examiner*—Patricia L Morris
(74) *Attorney, Agent, or Firm*—Birch, Stewart, Kolasch & Birch, LLP

(57) ABSTRACT

An acid addition salt of 3-(2-cyanophenyl)-5-(2-pyridyl)-1-phenyl-1,2-dihydropyridin-2-one or a hydrate thereof, wherein the acid is selected from the group consisting of benzenesulfonic acid, p-toluenesulfonic acid, hydrochloric acid, hydrobromic acid, sulfuric acid, methanesulfonic acid, fumaric acid, tartaric acid, succinic acid and benzoic acid.

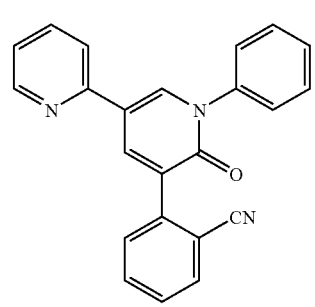

(1)

5 Claims, 11 Drawing Sheets

SALT OF 1,2-DIHYDROPYRIDINE COMPOUND

TECHNICAL FIELD

The present invention relates to 3-(2-cyanophenyl)-5-(2-pyridyl)-1-phenyl-1,2-dihydropyridin-2-one benzenesulfonate, p-toluenesulfonate, hydrochloride, hydrobromate, sulfate, methanesulfonate, fumarate, tartrate, succinate and benzoate useful as a therapeutic agent for Parkinson's disease and the like, having AMPA (α-amino-3-hydroxy-5-methyl-4-isooxazolepropionic acid) receptor antagonistic activity and/or kainic acid receptor inhibitory activity.

BACKGROUND ART

It is known that 1,2-dihydropyridine compounds including 3-(2-cyanophenyl)-5-(2-pyridyl)-1-phenyl-1,2-dihydropyridin-2-one have AMPA receptor antagonistic activity and/or kainic acid receptor inhibitory activity and are useful as therapeutic agents for Parkinson's disease and the like (see Patent Documents 1 and 2).

Example 7 of patent Document 1 and Example 1X of patent Document 2 discloses free forms of 3-(2-cyanophenyl)-5-(2-pyridyl)-1-phenyl-1,2-dihydropyridin-2-one. Patent Document 1 discloses "The compound according to (1), salts thereof or hydrates of the foregoing, which is any one of compounds selected from (snip), 3-(2-cyanophenyl)-5-(2-pyridyl)-1-phenyl-1,2-dihydropyridin-2-one, (snip)." (Patent Document 1, page 13, 13th line to page 20, 18th line); and for exemplary salts thereof, there has been made a general disclosure that "There is no particular limitation for "a salt" in the specification of the present application so far as it forms a salt with the compound of the present invention and is a pharmacologically acceptable one. Preferably, salt with a hydrogen halide (such as hydrofluoride, hydrochloride, hydrobromide or hydroiodide), salt with an inorganic acid (such as sulfate, nitrate, perchlorate, phosphate, carbonate or bicarbonate), salt with an organic carboxylic acid (such as acetate, trifluoroacetate, oxalate, maleate, tartrate, fumarate or citrate), salt with an organic sulfonic acid (such as methanesulfonate, trifluoromethanesulfonate, ethanesulfonate, benzenesulfonate, toluenesulfonate or camphor-sulfonate), salt with an amino acid (such as aspartate or glutamate), salt with a quaternary amine, salt with an alkaline metal (such as sodium salt or potassium salt) and salt with an alkaline earth metal (such as magnesium salt or calcium salt). More preferred examples of the "pharmacologically acceptable salt" are hydrochloride, oxalate, etc." (Patent Document 1, page 50, 9th line from bottom to page 51, 4th line).

However, although Patent Documents 1 and 2 disclose 3-(2-cyanophenyl)-5-(2-pyridyl)-1-phenyl-1,2-dihydropyridin-2-one, they do not describe any salt thereof in the context of a specific example.

[Patent Document 1] WO 01/96308
[Patent Document 2] WO 06/04107

DISCLOSURE OF THE INVENTION

Problem to be Solved by the Invention

One of the properties variable depending on the type of salts of medically useful compounds is the dissolution rate in a water medium. For oral forms, the dissolution rate of the medicament can affect the absorption rate of the active form of the medicament per se, the variation of absorption thereof and the like. Thus, the dissolution rate of the active form of the medicament is also one of important characteristics of pharmaceuticals for earlier exerting stable pharmacological activities. ("Iyakuhin no Kaihatsu (Development of Pharmaceuticals)" vol. 15, ed. Koichiro Miyajima, "Seizai no Butsurikagakuteki Seishitsu (Physicochemical Properties of Pharmaceutical Preparations)", p. 41 & 84, Tokyo, Hirokawa Shoten, Oct. 25, 1989; "Iyakuhin no Yoshutsu (Elution of Medicaments)", ed. J. T. Carstensen et al., p. 172-174, Chijinshokan Co., Ltd., Oct. 30, 1977).

In the industrial production of pharmaceuticals (particularly for production of an injection or liquid medicament), the medicament substance is desired to have suitable dissolution rate also for the maintenance of high quality and stable industrial productivity. Particularly, for example, in view of usability on medical site, it is necessary for the medicament substance to have reasonably high dissolution rate when employed in the form of an injection or liquid medicament prepared before use.

In this manner, the physical properties of medically useful compounds, salt thereof, and a crystal or amorphous form of the foregoing affect medicament bioavailability, medicament substance purity, production method, formulation preparations and the like. Thus, it is required in the development of pharmaceuticals to study which salt, crystal form or amorphous form of the compound is most excellent for pharmaceuticals.

However, because their physical properties depend on the attributes of the individual compound, it is difficult to predict a salt of a complex compound suitable for pharmaceuticals in view of physicochemical properties including dissolution rate, pharmacological activities, and the like. Thus, there is a need for the finding of various salts useful as pharmaceuticals for each compound.

Means for Solving the Problems

The present inventors have synthesized and isolated various salts of 3-(2-cyanophenyl)-5-(2-pyridyl)-1-phenyl-1,2-dihydropyridin-2-one (the compound represented by formula (I) below), followed by monitoring the physical properties and morphologies thereof for various studies. As a result, the inventors have found salts for the medicament substance, having favorable physical properties, thereby accomplishing the present invention.

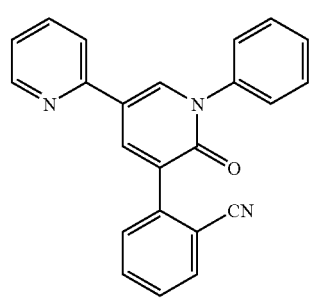

(1)

Specifically, the present invention relates to:

[1] An acid addition salt of 3-(2-cyanophenyl)-5-(2-pyridyl)-1-phenyl-1,2-dihydropyridin-2-one or a hydrate thereof, wherein the acid is selected from the group consisting of benzenesulfonic acid, p-toluenesulfonic acid, hydrochloric acid, hydrobromic acid, sulfuric acid, methanesulfonic acid, fumaric acid, tartaric acid, succinic acid and benzoic acid.

[2] 3-(2-cyanophenyl)-5-(2-pyridyl)-1-phenyl-1,2-dihydropyridin-2-one benzenesulfonate or a hydrate thereof;

[3] 3-(2-cyanophenyl)-5-(2-pyridyl)-1-phenyl-1,2-dihydropyridin-2-one p-toluenesulfonate or a hydrate thereof;

[4] 3-(2-cyanophenyl)-5-(2-pyridyl)-1-phenyl-1,2-dihydropyridin-2-one hydrochloride or a hydrate thereof;

[5] 3-(2-cyanophenyl)-5-(2-pyridyl)-1-phenyl-1,2-dihydropyridin-2-one hydrobromate or a hydrate thereof;

[6] 3-(2-cyanophenyl)-5-(2-pyridyl)-1-phenyl-1,2-dihydropyridin-2-one sulfate or a hydrate thereof;

[6-2] 3-(2-Cyanophenyl)-5-(2-pyridyl)-1-phenyl-1,2-dihydropyridin-2-one methanesulfonate or a hydrate thereof;

[6-3] 3-(2-cyanophenyl)-5-(2-pyridyl)-1-phenyl-1,2-dihydropyridin-2-one fumarate or a hydrate thereof.

[6-4] 3-(2-cyanophenyl)-5-(2-pyridyl)-1-phenyl-1,2-dihydropyridin-2-one tartrate or a hydrate thereof;

[6-5] 3-(2-cyanophenyl)-5-(2-pyridyl)-1-phenyl-1,2-dihydropyridin-2-one succinate or a hydrate thereof.

[6-6] 3-(2-cyanophenyl)-5-(2-pyridyl)-1-phenyl-1,2-dihydropyridin-2-one benzoate or a hydrate thereof.

[7] A pharmaceutical comprising the salt or a hydrate thereof as described in term [1] above;

[8] A pharmaceutical composition comprising the salt or a hydrate thereof as described in [1] above;

[9] A therapeutic agent for Parkinson's disease, Parkinsonian syndrome, epilepsy, or multiple sclerosis, comprising the salt or a hydrate thereof as described in [1] above;

[10] A therapeutic agent for Parkinson's disease, comprising the salt or a hydrate thereof as described in [1] above;

[11] A therapeutic agent for Parkinsonian syndrome, comprising the salt or a hydrate thereof as described in [1] above;

[12] A therapeutic agent for epilepsy, comprising the salt or a hydrate thereof as described in [1] above;

[13] A therapeutic agent for multiple sclerosis, comprising the salt or a hydrate thereof as described in [1] above, and the like.

EFFECTS OF THE INVENTION

Salts of 3-(2-cyanophenyl)-5-(2-pyridyl)-1-phenyl-1,2-dihydropyridin-2-one (hereinafter referred to as compound (1)) and hydrates thereof according to the present invention has excellent AMPA receptor antagonistic and/or kainic acid receptor inhibitory activity, further has excellent physical properties for medical use such as high dissolution rate in an aqueous solution, and is useful as a therapeutic agent for Parkinson's disease or the like.

BEST MODES FOR CARRYING OUT THE INVENTION

Figure 1:
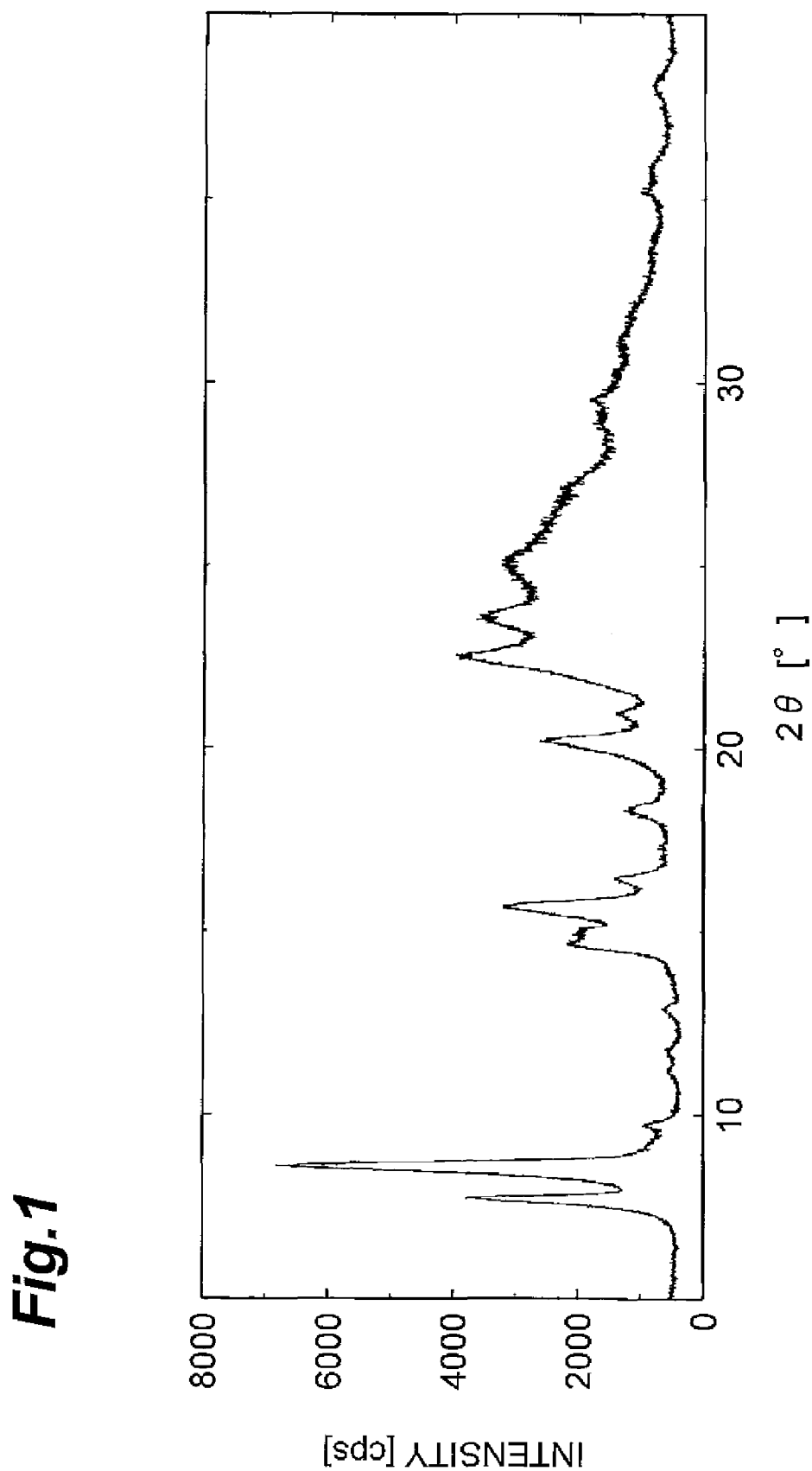
FIG. 1 is a powder X-ray diffraction pattern of the hydrochloride of compound (1), obtained in Example 1. The horizontal axis represents a diffraction angle (2θ), and the ordinate axis represents peak intensity.

Terms, symbols and the like as used herein are defined below, and the present invention will be described in detail.

An acid addition salt refers to a salt formed from a compound (1) and an acidic substance (inorganic or organic acid), and "acid addition salt of 3-(2-cyanophenyl)-5-(2-pyridyl)-1-phenyl-1,2-dihydropyridin-2-one" means a salt formed from 3-(2-cyanophenyl)-5-(2-pyridyl)-1-phenyl-1,2-dihydropyridin-2-one and an acidic substance (inorganic or organic acid).

A "salt" according to the present invention is not particularly limited so long as it is formed from compound (1) and an acid. By way of specific example, a salt is formed in an appropriate ratio of 0.1 to 5 molecules of an acid to 1 molecule of compound (1).

As used herein, salts of compound (1) or hydrates thereof may be present in crystalline polymorph (including crystalline pseudopolymorph) or amorphous form, and may be a crystalline polymorphous or amorphous form of any one of them or a mixture thereof. "A salt of compound (1) or a hydrate thereof" which is the present invention may refer to an anhydride or hydrate of the salt of compound (1), or a mixture thereof.

The compounds of the present invention can be produced by methods as described below. However, the method for producing a compound of the present invention is not intended to be limited to these methods.

The salts of compound (1) of the present invention can be produced by the following method.

Compound (1) can be synthesized according to a method as described in the above-mentioned Patent Document 1 or 2.

Compound (1) used for producing the salt can be in any form, i.e. can be hydrate or anhydride form, amorphous or crystalline form (including plural crystal polymorphs), or a mixture thereof.

When producing the salt of compound (1), compound (1), an acid, and a solvent are mixed. The order in which compound (1), the acid, and the solvent are added is not limited, and they may be each added in installments.

Here, compound (1) may be added in solid form, or be added in the form of a mixture of the compound and solvent (in the state of a solution, suspension, slurry or the like).

The acid used for producing the salt may be added by bubbling an acidic gas such as hydrogen chloride into the solution, be added in the form of an acidic liquid such as concentrated sulfuric acid and methanesulfonic acid or a solid acid substance without dissolution in the solution, or be added in the form of an acidic solution in which the acidic gas, solid acid substance or acidic liquid is dissolved in water or an organic solvent.

After mixing compound (1) and acid, the mixture is subjected to stirring, standing or distilling-off of the solvent to precipitate a salt of compound (1). The precipitated salt can be separated by conventional filtering operation, washed, if necessary, with a suitable solvent (typically identical to the solvent used for the precipitation), and further dried to provide a salt of the compound of the present invention.

Alternatively, the salt of compound (1) and the acid is once formed as described above, further again mixed with the solvent, and subjected to stirring, standing or distilling-off of the solvent to precipitate the salt of compound (1). The precipitated salt can be separated by conventional filtering operation, washed, if necessary, with a suitable solvent (typically identical to the solvent used for the precipitation), and further dried to provide the salt of the compound of the present invention.

Non-limiting examples of the solvent used for producing the salt typically include ketones such as methyl ethyl ketone and acetone; alcohols such as methanol, ethanol, isopropanol and n-propanol; esters such as ethyl acetate and methyl acetate; hydrocarbons such as hexane and heptane; ethers such as tetrahydrofuran, diethyl ether and dioxane; carboxylic acids such as acetic acid; or water or mixed solvents thereof. The amount of the solvent used may be properly selected between the lower limit and the upper limit, the lower limit being an amount to dissolve compound (1) and each acid to be mixed (for example, in the state of a solution, suspension or slurry) by heating and the upper limit being an amount so as not to significantly reduce the yield of the salt. The temperature at which the compound (1) and each acid are mixed may be properly selected depending on the solvent. The final cooling temperature may be properly selected in view of the yield, quality or the like of the salt; and it is preferably from room temperature to 0° C.

Alternatively, a poor solvent (for example, hexane, heptane and the like) may be added to a solution in which compound (1) and each acid are mixed to precipitate the salt of the present invention.

The salt separated by the filtration can be dried by allowing it to stand in the atmosphere, but it is not effective for large scale production, therefore drying by heating is preferable. Drying temperature may appropriately be selected depending on the production quantity. Drying time may properly be selected as the time during which the residual solvent is removed below the prescribed amount depending on the production quantity, drying apparatus, drying temperature or the like. Drying can be performed either under aeration or under reduced pressure, and drying under reduced pressure is preferable. The level of pressure reduction may appropriately be selected, depending on the production quantity, drying apparatus, drying temperature or the like.

The use of compound (1) as a therapeutic agent for Parkinson's disease or the like is disclosed in detail in Patent Documents 1 and 2; similarly, salts or hydrates thereof according to the present invention can be used as an active ingredient of a therapeutic agent for Parkinson's disease or the like.

When a salt or a hydrate thereof according to the present invention is used as a medicament, the salt or the hydrate thereof according to the present invention is generally mixed with a suitable additive and formulated. However, this does not negate the direct use of the salt or the hydrate thereof according to the present invention as a medicament.

Examples of the additive can include additives typically used in pharmaceuticals, such as excipients, binders, lubricants, disintegrators, coloring agents, taste correctives, emulsifiers, surfactants, dissolving aids, suspending agents, isotonizing agents, buffering agents, antiseptic agents, antioxidants, stabilizers, absorption accelerators and the like. These additives may be also used, if desired, in proper combination.

Examples of the excipient can include lactose, saccharose, glucose, corn starch, mannitol, sorbitol, starch, pregelatinized starch, dextrin, crystalline cellulose, light anhydrous silicic acid, aluminum silicate, calcium silicate, magnesium aluminometasilicate, calcium hydrogen phosphate and the like.

Examples of the binder can include polyvinyl alcohol, methylcellulose, ethylcellulose, gum arabic, tragacanth, gelatin, shellac, hydroxypropylmethylcellulose, hydroxypropylcellulose, carboxymethylcellulose sodium, polyvinylpyrrolidone, macrogol and the like.

Examples of the lubricant can include magnesium stearate, calcium stearate, sodium stearyl fumarate, talc, polyethylene glycol, colloidal silica and the like.

Examples of the disintegrator can include crystalline cellulose, agar, gelatin, calcium carbonate, sodium bicarbonate, calcium citrate, dextrin, pectin, low-substituted hydroxypropylcellulose, carboxymethyl cellulose, carboxymethylcellulose calcium, croscarmellose sodium, carboxymethyl starch, carboxymethyl starch sodium and the like.

Examples of the coloring agent can include coloring agent being approved for addition to pharmaceuticals such as iron sesquioxide, yellow iron sesquioxide, carmine, caramel, α-carotene, titanium oxide, talc, riboflavin sodium phosphate, yellow aluminum lake and the like.

Examples of the taste corrective can include cocoa powder, menthol, aromatic powder, peppermint oil, camphor, cinnamon powder and the like.

Examples of the emulsifier or surfactant can include stearyl triethanolamine, sodium lauryl sulfate, laurylaminopropionic acid, lecithin, glyceryl monostearate, sucrose fatty acid ester, glycerine fatty acid ester and the like.

Examples of the dissolving aid can include polyethylene glycol, propylene glycol, benzyl benzoate, ethanol, cholesterol, triethanolamine, sodium carbonate, sodium citrate, polysorbate 80, nicotinic acid amide and the like.

Examples of the suspending agent can include, in addition to the above surfactants, hydrophilic polymers such as polyvinyl alcohol, polyvinylpyrrolidone, methylcellulose, hydroxymethylcellulose, hydroxyethylcellulose, hydroxypropylcellulose and the like.

Examples of the isotonizing agent can include glucose, sodium chloride, mannitol, sorbitol and the like.

Examples of the buffering agent can include buffering solutions such as phosphate, acetate, carbonate, citrate and the like.

Examples of the antiseptic agent can include methylparaben, propylparaben, chlorobutanol, benzyl alcohol, phenethyl alcohol, dehydroacetic acid, sorbic acid and the like.

Examples of the antioxidant can include sulfite, ascorbic acid, α-tocopherol and the like.

Examples of the stabilizer can include those typically used in pharmaceuticals.

Examples of the absorption accelerator can include those typically used in pharmaceuticals.

Examples of the preparation can include oral forms such as tablets, powders, granules, capsules, syrups, lozenges and inhalants; external forms such as suppositories, ointments, eye salves, tapes, eye drops, nose drops, ear drops, poultices, lotions and the like; and injections.

The oral forms are each obtained by formulation using a proper combination of the above additives. The surface thereof may be coated, if necessary.

The external forms are each obtained by formulation using a proper combination of the above-described additives, in particular, excipients, binders, taste correctives, emulsifiers, surfactants, dissolving aids, suspending agents, isotonizing agents, antiseptic agents, antioxidants, stabilizers and absorption accelerators.

The injections are each obtained by formulation using a proper combination of the above-described additives, in particular, emulsifiers, surfactants, dissolving aids, suspending agents, isotonizing agents, buffering agents, antiseptic agents, antioxidants, stabilizers and absorption accelerators.

When a salt or a hydrate thereof according to the present invention is used as a medicament, the usage amount varies depending on symptoms and ages; however, a salt or a hydrate thereof is typically used at a dose of 0.1 to 30 mg/day/individual (preferably 0.5 to 10 mg/day/individual) for an oral form and at a dose of 0.1 to 10 mg/day/individual for an injection, and may be administered once daily, or twice to six times daily in divided doses for both of the oral form and injection. For an external form, a salt or a hydrate thereof is used at a dose of 0.5 to 40 mg per administration and can be employed once or several times daily or once for 1 to 10 days.

In this respect, the dose indicates the value of the amount actually administered for the oral form and injection and the value of the amount actually absorbed by the body for the external form.

A preparation containing a salt of compound (1) or a hydrate thereof which is the present invention, for use in therapy on humans can be obtained by a pharmaceutically commonly used method such as pharmaceutical formulation as described in Patent Document 2.

EXAMPLES

Compound (1) of the present invention can be produced, for example, by a method as described in Examples below. In addition, the effect of the compound can be identified by a method as described in the following Test Example. However, these methods are illustrative, and the present invention is not intended to be limited to the following specific examples in any manner; changes may be made in the range not departing from the scope of the present invention.

Example 1

3-(2-Cyanophenyl)-5-(2-pyridyl)-1-phenyl-1,2-dihydropyridin-2-one hydrochloride

A mixture of 3-(2-cyanophenyl)-5-(2-pyridyl)-1-phenyl-1,2-dihydropyridin-2-one hydrate (4.73 g, 3.25 mmol) and ethanol (small amount) was concentrated under reduced pressure, followed by adding ethyl acetate (small amount) to the residue before further concentration under reduced pressure. A 4N—HCl/ethyl acetate solution (3.9 mL, 15.6 mmol) was added to an ethyl acetate (80 mL) suspension containing the resultant residue, which was then stirred at room temperature for 3.5 hours. The precipitated solid was collected by filtration, washed with ethyl acetate (small amount), and then dried under reduced pressure to provide 4.64 g of the title compound as pale yellow crystals. (It was identified by Karl Fischer method that the crystal had a water content of 1.6%).

$^1$H-NMR (400 MHz, DMSO-$d_6$) δ 8.65 (d, J=4.8 Hz, 1H), 8.62 (d, J=2.8 Hz, 1H), 8.47 (d, J=2.8 Hz, 1H), 8.15 (d, J=8.0 Hz, 1H), 8.03-8.10 (m, 1H), 7.93 (dd, J=1.2, 7.2 Hz, 14), 7.79 (dt, J=1.2, 7.2 Hz, 1H), 7.74 (d, J=7.2 Hz, 114), 7.46-7.55 (m, 5H), 7.46-7.55 (m, 2H).

Example 2

3-(2-Cyanophenyl)-5-(2-pyridyl)-1-phenyl-1,2-dihydropyridin-2-one hydrobromate

A mixture of 3-(2-cyanophenyl)-5-(2-pyridyl)-1-phenyl-1,2-dihydropyridin-2-one hydrate (4.73 g, 3.25 mmol) and ethanol (small amount) was concentrated under reduced pressure, followed by adding ethyl acetate (small amount) to the residue before further concentration under reduced pressure. A 25% HBr/acetic acid solution (1.04 g, 4.2 mmol) was added to an ethyl acetate (30 mL) suspension containing the resultant residue, which was then stirred at room temperature for 3.5 hours. The precipitated solid was collected by filtration, washed with ethyl acetate (small amount), and then dried under reduced pressure to provide 1.28 g of the title compound as pale yellow crystals.

$^1$H-NMR (400 MHz, DMSO-$d_6$) δ 8.63 (d, J=4.0 Hz, 1H), 8.56 (d, J=2.8 Hz, 1H), 8.46 (d, J=2.8 Hz, 1H), 8.08 (d, J=8.0 Hz, 1H), 7.91-7.99 (m, 2H), 7.79 (dt, J=1.2, 7.2 Hz, 1H), 7.72 (d, J=7.2 Hz, 1H), 7.46-7.55 (m, 5H), 7.48-7.54 (m, 1H), 7.38-7.43 (m, 1H).

Example 3

3-(2-Cyanophenyl)-5-(2-pyridyl)-1-phenyl-1,2-dihydropyridin-2-one sulfate

A mixture of 3-(2-cyanophenyl)-5-(2-pyridyl)-1-phenyl-1,2-dihydropyridin-2-one (1.0 g, 0.687 mmol) and ethanol (small amount) was concentrated under reduced pressure, followed by adding ethyl acetate (small amount) to the residue before further concentration under reduced pressure. A 10% (v/v) $H_2SO_4$/ethyl acetate solution (0.439 mL, 0.824 mmol) was added to an ethyl acetate (15 mL) suspension containing the resultant residue, which was then stirred at room temperature for 4 days. The precipitated solid was collected by filtration, washed with ethyl acetate (small amount), and then dried under reduced pressure to provide 475 mg of the title compound as white crystals.

¹H-NMR (400 MHz, DMSO-d₆) δ 8.61 (d, J=4.8 Hz, 1H), 8.55 (d, J=2.8 Hz, 1H), 8.46 (d, J=2.8 Hz, 1H), 8.06 (d, J=8.0 Hz, 1H), 7.89-7.96 (m, 2H), 7.79 (dt, J=1.2, 7.2 Hz, 1H), 7.72 (dd, J=1.2, 7.2 Hz, 1H), 7.56-7.62 (m, 5H), 7.48-7.54 (m, 1H), 7.35-7.40 (m, 1H).

Example 4

3-(2-Cyanophenyl)-5-(2-pyridyl)-1-phenyl-1,2-dihydropyridin-2-one sulfate

A mixture of concentrated sulfuric acid (60 μL, 1.08 mmol) and tetrahydrofuran (5 mL) was added under cooling with ice to a mixture of 3-(2-cyanophenyl)-5-(2-pyridyl)-1-phenyl-1,2-dihydropyridin-2-one (200 mg, 0.138 mmol) and tetrahydrofuran (20 mL), which was then stirred under cooling with ice for one hour. The precipitated solid was collected by filtration, washed with ethyl acetate (small amount), and then dried under reduced pressure to provide 212 mg of the title compound as white crystals.
¹H-NMR (400 MHz, DMSO-d₆) δ 8.64 (d, J=4.0 Hz, 1H), 8.57 (d, J=2.8 Hz, 1H), 8.45 (d, J=2.8 Hz, 1H), 8.10 (d, J=8.0 Hz, 1H), 7.96-8.10 (m, 2H), 7.93 (d, J=8.0 Hz, 1H), 7.79 (dt, J=1.2, 7.2 Hz, 1H), 7.72 (d, J=7.2 Hz, 1H), 7.56-7.62 (m, 5H), 7.49-7.55 (m, 1H), 7.40-7.45 (m, 1H).

Example 5

3-(2-Cyanophenyl)-5-(2-pyridyl)-1-phenyl-1,2-dihydropyridin-2-one benzenesulfonate A benzenesulfonic acid aqueous solution (1 mL, containing 2.02 mmol benzenesulfonic acid) was added to a mixture of 3-(2-cyanophenyl)-5-(2-pyridyl)-1-phenyl-1,2-dihydropyridin-2-one (506 mg, 1.40 mmol) and acetone (5 mL), which was then heated to reflux in an oil bath for complete dissolution. Isopropanol (20 mL) was added to the mixture, which was then stirred at 60° C. for 40 minutes and subsequently allowed to stand for 13 hours in an oil bath, the heating of which was stopped. This mixture was then allowed to stand at 5° C. for 2 hours followed by collecting the precipitated solid by filtration. The resultant precipitate was dried with aeration at 60° C. for 3 hours to provide 442 mg of the title compound as pale yellow crystals.

Example 6

3-(2-Cyanophenyl)-5-(2-pyridyl)-1-phenyl-1,2-dihydropyridin-2-one p-toluenesulfonate A p-toluenesulfonic acid aqueous solution (1.25 mL, containing 1.97 mmol p-toluenesulfonic acid) and isopropanol (30 mL) were added to a mixture of 3-(2-cyanophenyl)-5-(2-pyridyl)-1-phenyl-1,2-dihydropyridin-2-one (532 mg, 1.47 mmol) and acetone (5 mL), which was then stirred at 80° C. (in an oil bath). Purified water (2.25 mL) was added to the mixture before filtration. The filtrate was again heated to 80° C. and then allowed to stand for 13 hours in an oil bath, the heating of which was stopped. This mixture was then allowed to stand at 5° C. for 5 hours, followed by collecting the precipitated solid by filtration. The obtained precipitate was dried with aeration at 60° C. for about 3 hours to provide 483 mg of the title compound as pale yellow crystals.

Example 7

3-(2-Cyanophenyl)-5-(2-pyridyl)-1'-phenyl-1,2-dihydropyridin-2-one methanesulfonate Methanesulfonic acid (0.04 mL) was added at room temperature to a mixture of 3-(2-cyanophenyl)-5-(2-pyridyl)-1-phenyl-1,2-dihydropyridin-2-one hydrate (900 mg) and ethyl acetate (30 mL). Acetone (30 mL) was added to this mixture, which was then stirred at room temperature for 10 minutes and subsequently concentrated under reduced pressure. Ethyl acetate was added to the residue to make a suspension. The precipitate in the mixture was collected by filtration and then washed with ethyl acetate to provide 410 mg of the title compound.
¹H-NMR (400 MHz, CDCl₃) δ 2.79 (s, 0.3-0.5), 7.42-7.62 (m, 7H), 7.66 (ddd, J=7.6, 7.6, 1.6 Hz, 1H), 7.75-7.85 (m, 3H), 8.04 (brs, 1H), 8.21 (brd, J=2.4 Hz, 1H), 8.47 (brs, 1H), 8.85 (brs, 1H).

Example 8

3-(2-Cyanophenyl)-5-(2-pyridyl)-1'-phenyl-1,2-dihydropyridin-2-one fumarate

Isopropyl acetate (15.5 mL) was added to 3-(2-cyanophenyl)-5-(2-pyridyl)-1-phenyl-1,2-dihydropyridin-2-one hydrate (256.80 mg, 0.71 mmol), and completely resolved under reflux by using oil bath. Then, methanol solution of fumaric acid (5 mL, containing 0.75 mmol of fumaric acid) was added, solid was precipitated at 85° C., and subsequently allowed to stand for about 17 hours in an oil bath, the heating of which was stopped. The obtained solid was collected by filtration, washed by n-octane (small amount), dried under reduced pressure at 60° C., for 5 hours to provide 263.84 mg of the title compound as slightly yellowish white crystals.

Example 9

3-(2-Cyanophenyl)-5-(2-pyridyl)-1-phenyl-1,2-dihydropyridin-2-one tartrate

Methyl ethyl ketone (7 mL) was added to 3-(2-cyanophenyl)-5-(2-pyridyl)-1-phenyl-1,2-dihydropyridin-2-one hydrate (258.17 mg, 0.71 mmol), and completely resolved under reflux by using oil bath. Then, tetrahydrofuran solution of L(+)-tartaric acid (6 mL, containing 0.77 mmol of tartaric acid) was added, and the heating of the oil bath was stopped. Then, n-octane (22 mL) was added to the mixture, solid was precipitated, and subsequently allowed to stand for about 13 hours and a half in the oil bath. The obtained solid was collected by filtration, washed by n-octane (small amount), dried under reduced pressure at 60° C., for about 5 hours to provide 283.86 mg of the title compound as white crystals.

Example 10

3-(2-Cyanophenyl)-5-(2-pyridyl)-1-phenyl-1,2-dihydropyridin-2-one succinate

Acetonitrile (5 mL) was added to 3-(2-cyanophenyl)-5-(2-pyridyl)-1-phenyl-1,2-dihydropyridin-2-one hydrate (255.2 mg, 0.70 mmol), and completely resolved under reflux by using oil bath. Then, methanol solution of succinic acid (2 mL, containing 0.77 mmol of succinic acid) was added, heating of the oil bath was stopped, brought out from the oil bath, and subsequently allowed to stand at room temperature.

The mixture returning to the room temperature was transferred to a weighing bottle and allowed to stand for about 15 hours. The solid precipitated was dried under reduced pressure at 60° C. for about 4 hours to provide 299.03 mg of the title compound as slightly yellowish white crystals.

Example 11

3-(2-Cyanophenyl)-5-(2-pyridyl)-1-phenyl-1,2-dihydropyridin-2-one benzoate

Methyl ethyl ketone (6 mL) was added to 3-(2-cyanophenyl)-5-(2-pyridyl)-1-phenyl-1,2-dihydropyridin-2-one hydrate (253.6 mg, 0.70 mmol), and completely resolved under reflux by using oil bath. Then, tetrahydrofuran solution of benzoic acid (1 mL, containing 0.75 mmol of benzoic acid) was added, the heating of the oil bath was stopped, brought out from the oil bath, and subsequently allowed to stand at room temperature. The mixture returning to the room temperature was transferred to a weighing bottle and allowed to stand for about 15 hours in hood. The solid precipitated was dried under reduced pressure at 60° C. for about 4 hours to provide 249.81 mg of the title compound as slightly yellowish white crystals.

Measurement of Powder X-Ray Diffraction Pattern

The powder X-ray diffraction of the crystals obtained in each Example were measured under the following measurement conditions according to the powder X-ray diffraction measurement method described in General Tests, Japanese Pharmacopeia.

Examples 1 to 7

Condition 1

(Equipment)
Powder X-ray diffraction measurement apparatus: RINT-2000 (from Rigaku Corporation)

(Operation Procedure)
A sample was pulverized using an agate mortar, taken on a glass plate having a diameter of 13 mm, and measured under the following conditions.

X-ray used: CuKα ray

Tube voltage: 40 kV

Tube current: 200 mA

Divergence slit: ½ deg

Receiving slit: 0.3 mm

Scattering slit: ½ deg

Scanning rate: 1°/min.

Scanning step: 0.01°

Measurement range ($2\theta$): 5 to 40°

Examples 8 to 11

Condition 2

(Equipment)
Powder X-ray diffraction measurement apparatus: TTR-III (from Rigaku Corporation)

(Operation Procedure)
A sample was pulverized using an agate mortar, taken on an aluminum pan for measurement, and measured under the following conditions.

X-ray used: CuKα ray

Tube voltage: 50 kV

Tube current: 300 mA

Divergence slit: 0.50 mm

Divergence longitudinal restriction slit: 2 mm

Receiving slit: open

Scattering slit: open

Scanning rate: 2°/min

Scanning step: 0.02°

Measurement range ($2\theta$): 2 to 40°

Figure 2:
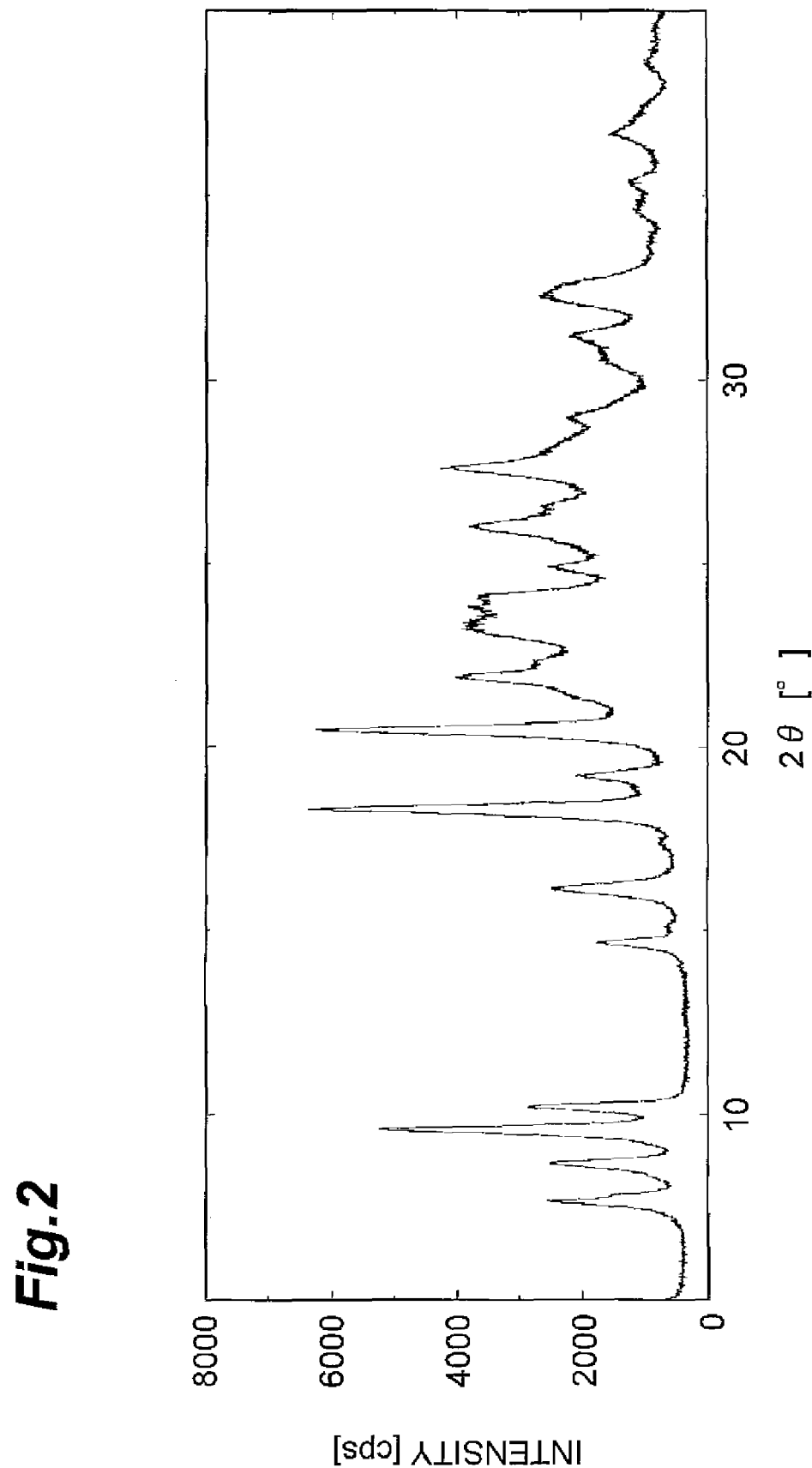
FIG. 2 is a powder X-ray diffraction pattern of the hydrobromate of compound (1), obtained in Example 2. The horizontal axis represents a diffraction angle (2θ), and the ordinate axis represents peak intensity.
Figure 3:
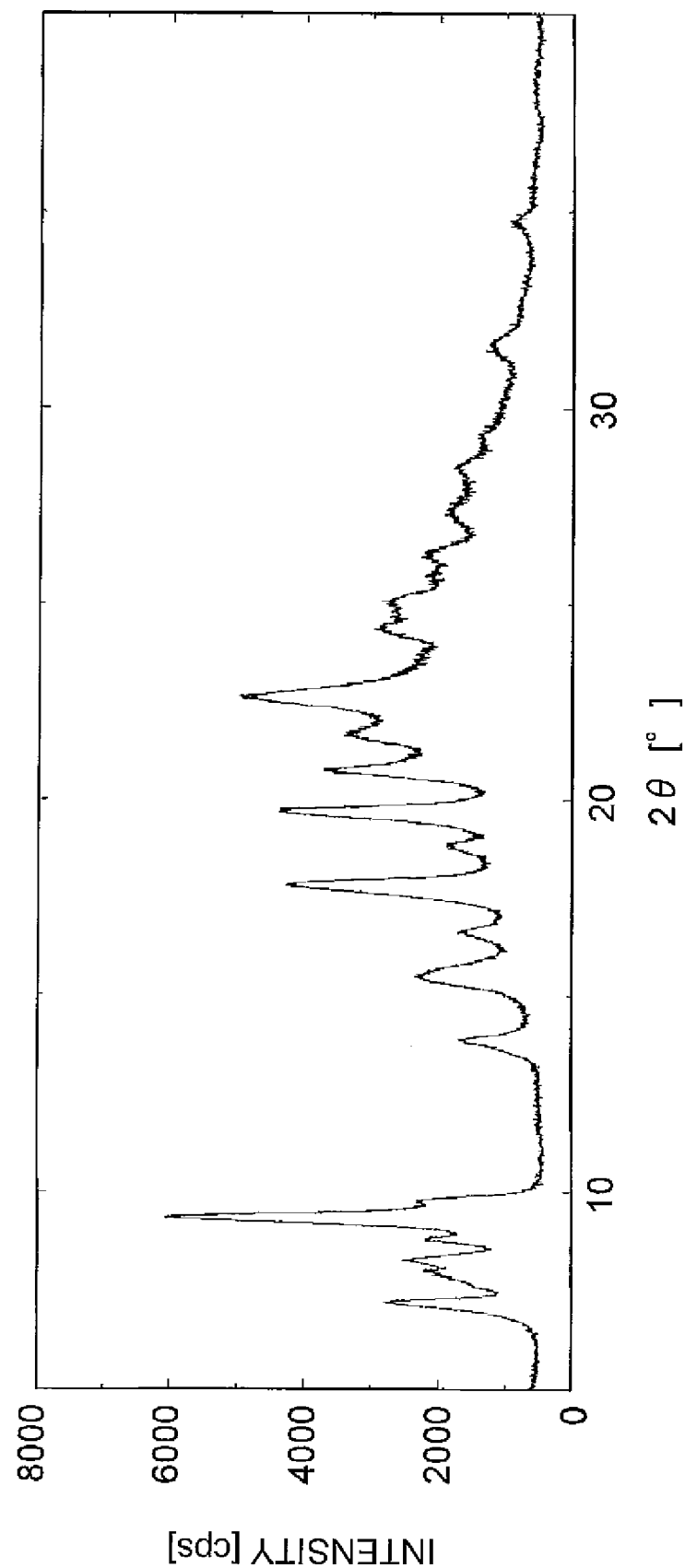
FIG. 3 is a powder X-ray diffraction pattern of the sulfate of compound (1), obtained in Example 3. The horizontal axis represents a diffraction angle (2θ), and the ordinate axis represents peak intensity.
Figure 4:
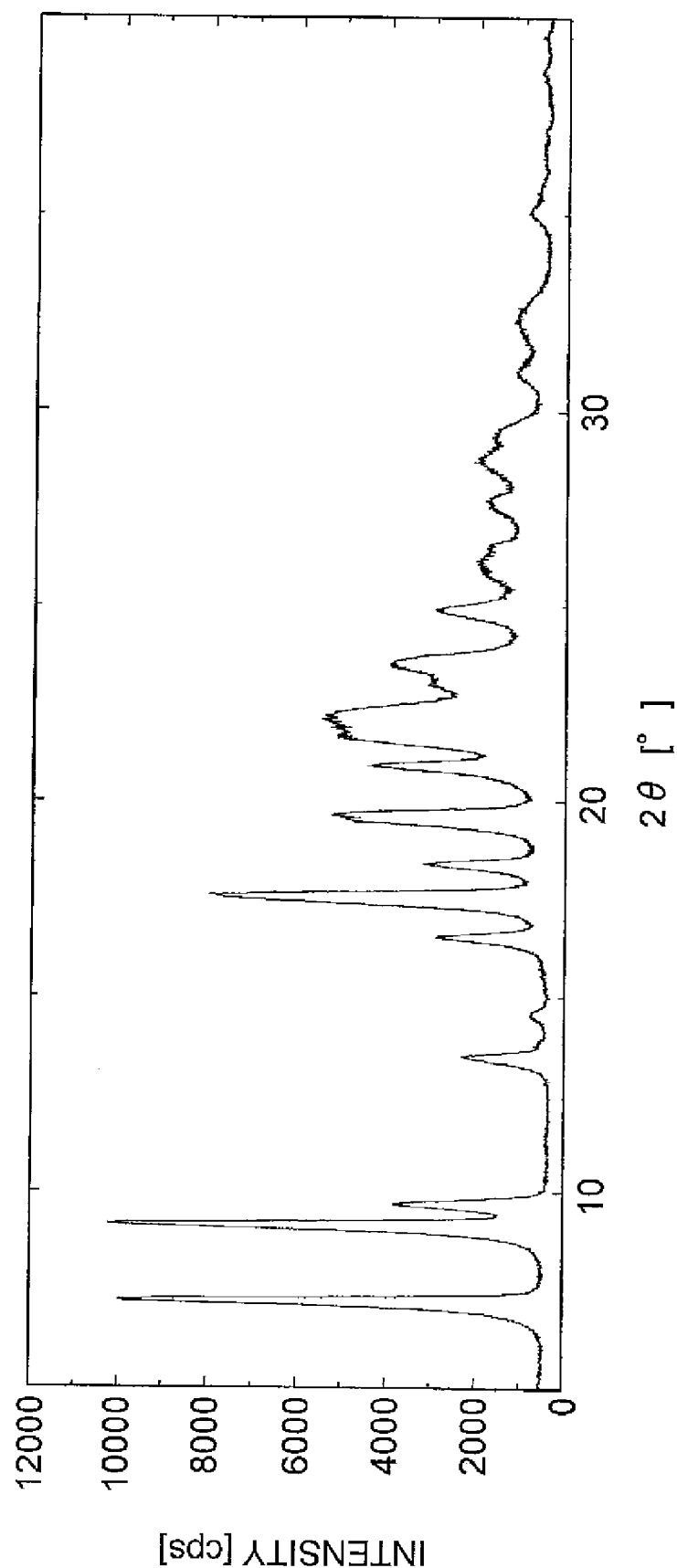
FIG. 4 is a powder X-ray diffraction pattern of the sulfate of compound (1), obtained in Example 4. The horizontal axis represents a diffraction angle (2θ), and the ordinate axis represents peak intensity.
Figure 5:
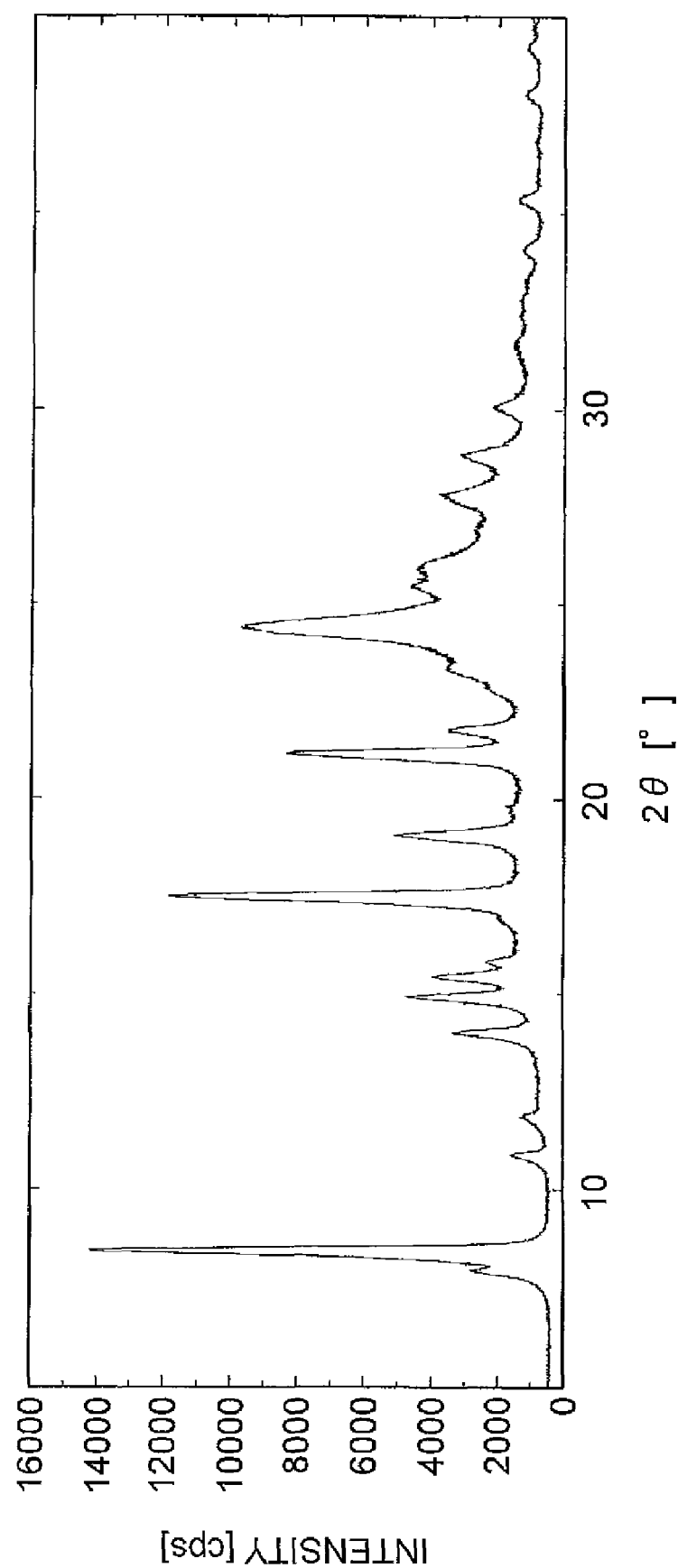
FIG. 5 is a powder X-ray diffraction pattern of the benzenesulfonate of compound (1), obtained in Example 5. The horizontal axis represents a diffraction angle (2θ), and the ordinate axis represents peak intensity
Figure 6:
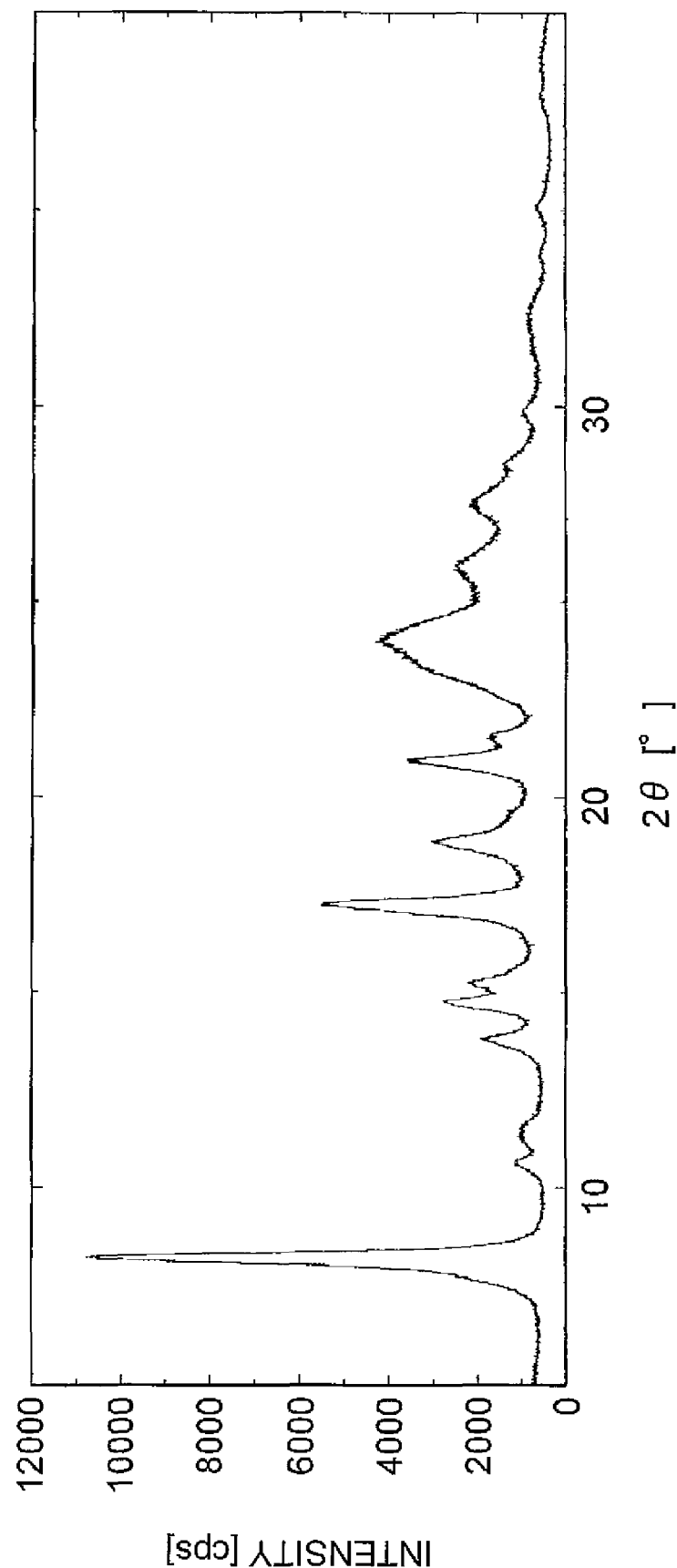
FIG. 6 is a powder X-ray diffraction pattern of the p-toluenesulfonate of compound (1), obtained in Example 6. The horizontal axis represents a diffraction angle (2θ), and the ordinate axis represents peak intensity
Figure 7:
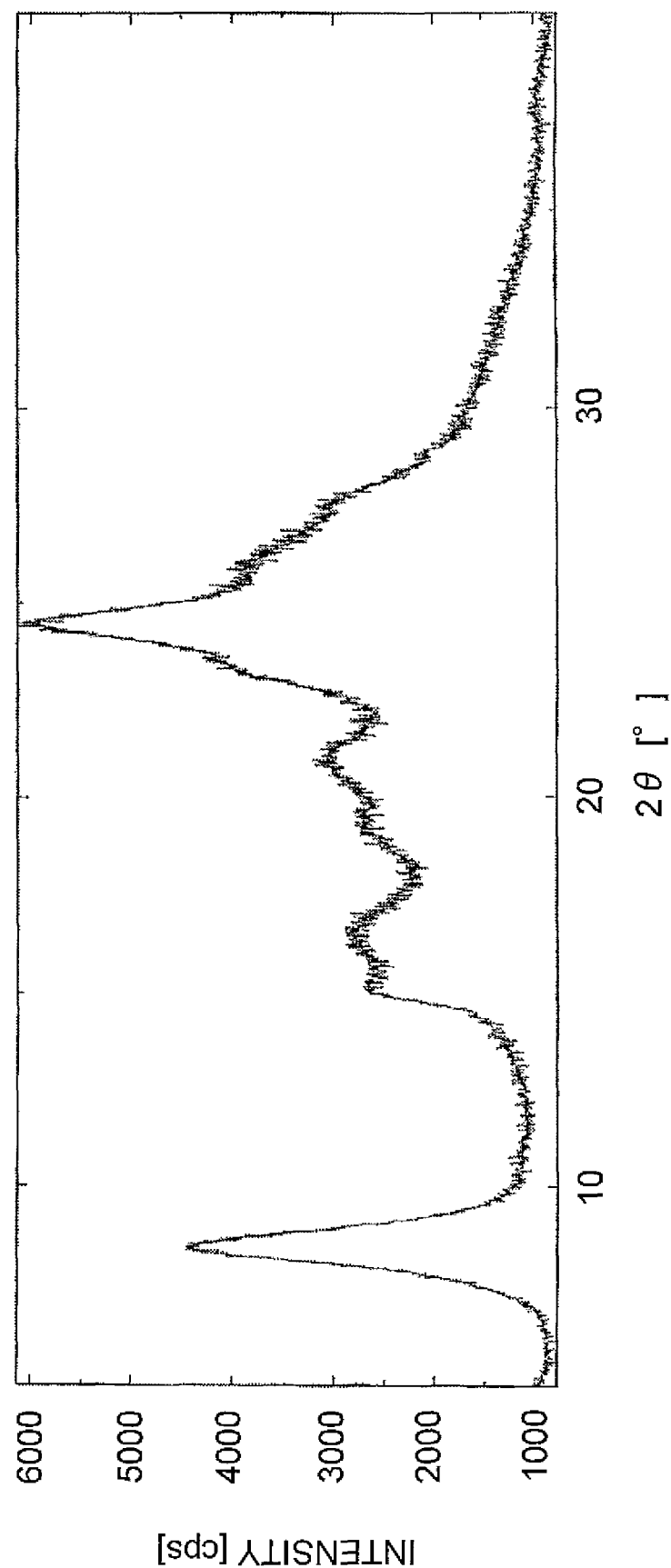
FIG. 7 is a powder X-ray diffraction pattern of the methanesulfonate of compound (1), obtained in Example 7. The horizontal axis represents a diffraction angle (2θ), and the ordinate axis represents peak intensity.
Figure 8:
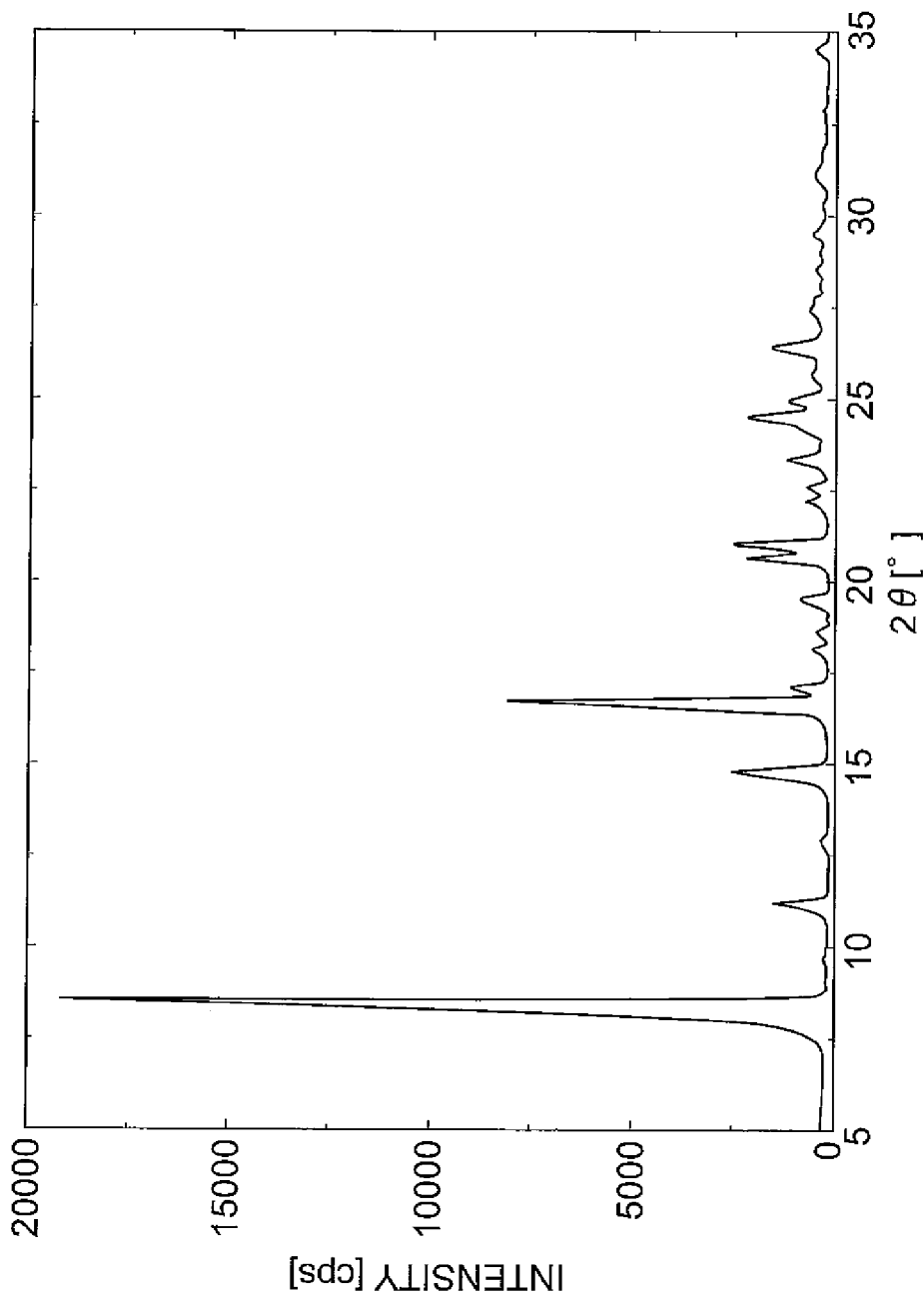
FIG. 8 is a powder X-ray diffraction pattern of the fumarate of compound (1), obtained in Example 8. The horizontal axis represents a diffraction angle (2θ), and the ordinate axis represents peak intensity.
Figure 9:
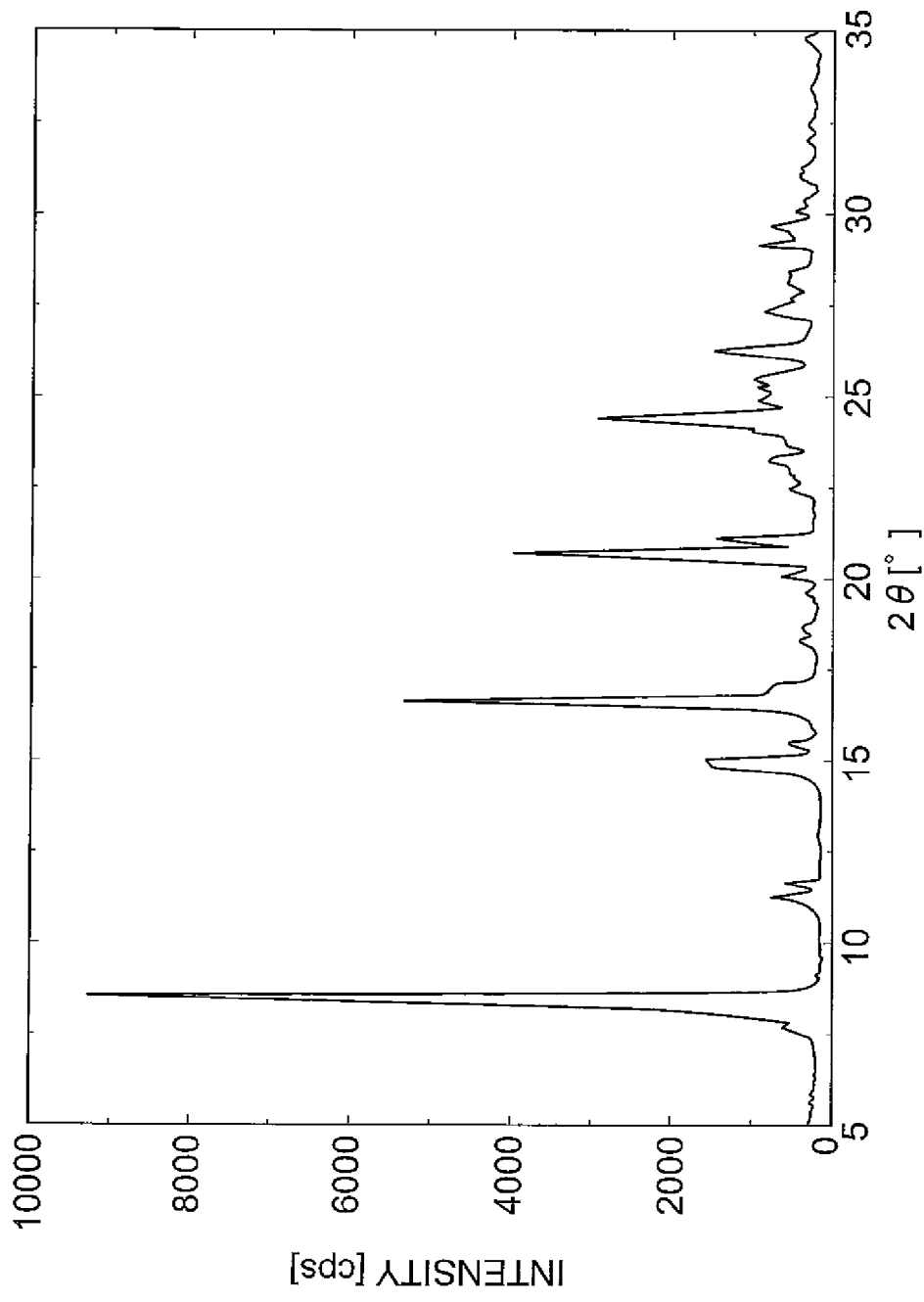
FIG. 9 is a powder X-ray diffraction pattern of the tartrate of compound (1), obtained in Example 9. The horizontal axis represents a diffraction angle (2θ), and the ordinate axis represents peak intensity.
Figure 10:
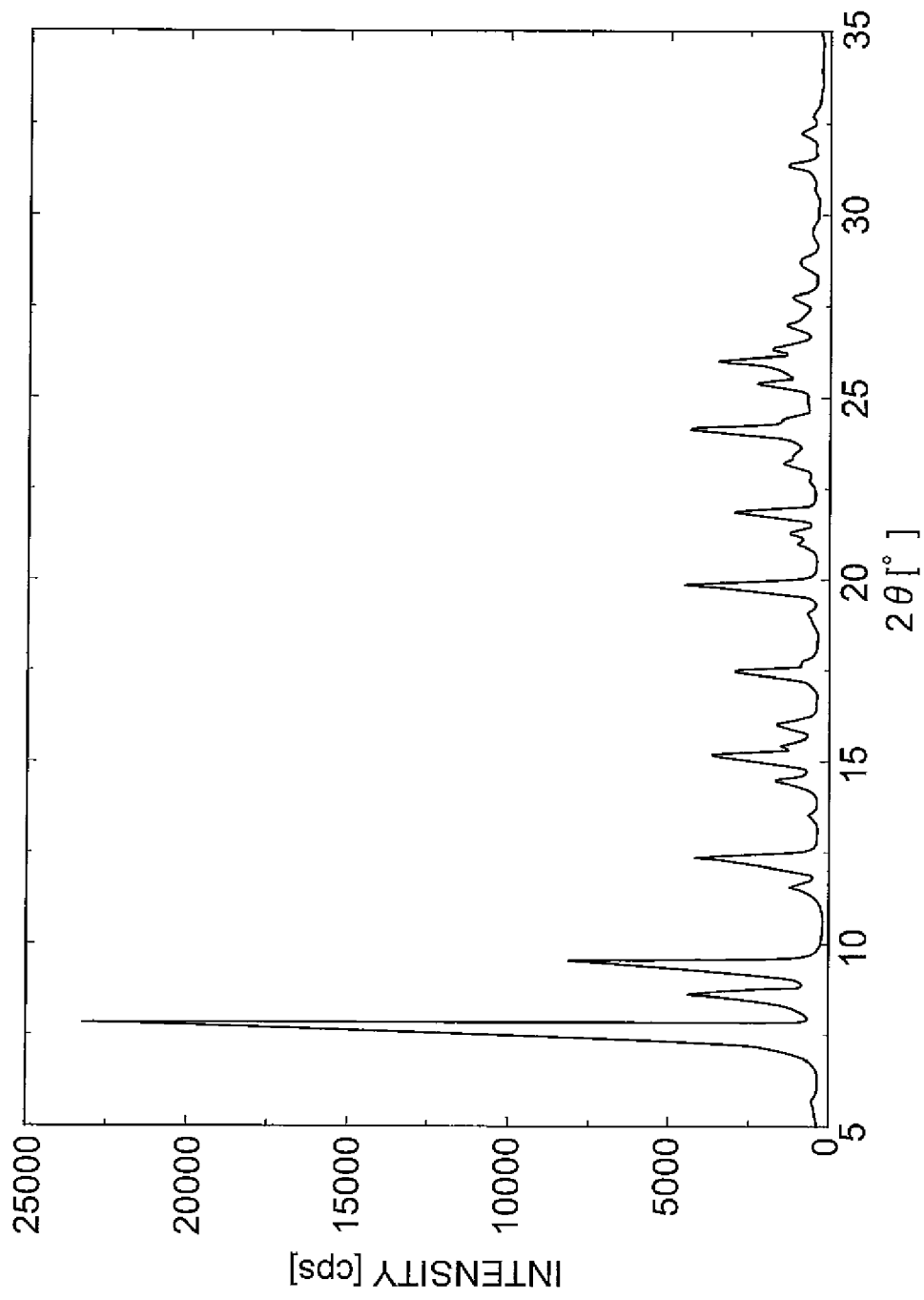
FIG. 10 is a powder X-ray diffraction pattern of the succinate of compound (1), obtained in Example 10. The horizontal axis represents a diffraction angle (2θ), and the ordinate axis represents peak intensity.
Figure 11:
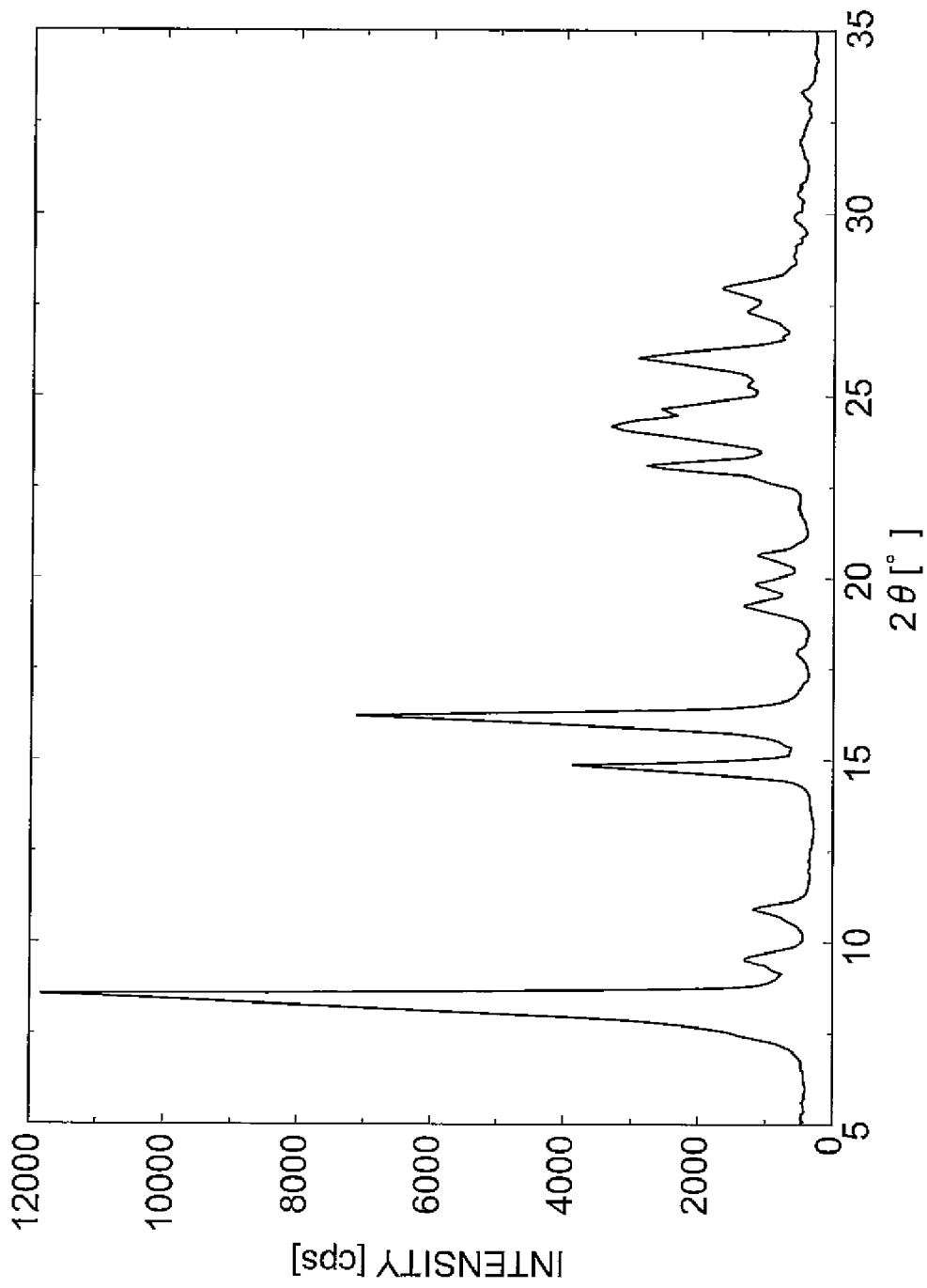
FIG. 11 is a powder X-ray diffraction pattern of the benzoate of compound (1), obtained in Example 11. The horizontal axis represents a diffraction angle (2θ), and the ordinate axis represents peak intensity.

The powder X-ray diffraction patterns of the salts obtained in Example 1 are shown in FIG. 1, the powder X-ray diffraction patterns of the salts obtained in Example 2 are shown in FIG. 2, the powder X-ray diffraction patterns of the salts obtained in Example 3 are shown in FIG. 3, the powder X-ray diffraction patterns of the salts obtained in Example 4 are shown in FIG. 4, the powder X-ray diffraction patterns of the salts obtained in Example 5 are shown in FIG. 5, the powder X-ray diffraction patterns of the salts obtained in Example 6 are shown in FIG. 6, the powder X-ray diffraction patterns of the salts obtained in Example 7 are shown in FIG. 7, the powder X-ray diffraction patterns of the salts obtained in Example 8 are shown in FIG. 8, the powder X-ray diffraction patterns of the salts obtained in Example 9 are shown in FIG. 9, the powder X-ray diffraction patterns of the salts obtained in Example 10 are shown in FIG. 10, and the powder X-ray diffraction patterns of the salts obtained in Example 11 are shown in FIG. 11.

Test Example 1

Test Method for Measuring Dissolution Rate

[Method]
The dissolution rates of the each salt of compound (1) (Examples 1, 2, 3, 5, 6, 7, 8, 9, 10 and 11) were measured under the following conditions using a rotating disc method (see J. H. Wood et al., J. Pharm. Soc., 54: 1068 (1965)). Sample solutions were timely taken, and the concentration thereof was measured under HPLC conditions as described below. The dissolution rate was then calculated, by regression analysis, based on the range in which linearity was maintained in the relationship between the measuring time and the concentration.

(Conditions for the Rotating Disc Method)

Solvents: "1st fluid" (pH 1.2) (hereinafter referred to as JP1 fluid) and "2nd fluid" (pH 6.8) (hereinafter referred to as JP2 fluid) as described in General Tests (disintegration test) of Japanese Pharmacopeia Amount of solvent: 500 mL Disc molding pressure: 2 tons Temperature: 37° C.

Disk rotation speed: 50 rpm

Area of powder contacting with solvent on disc: 1 cm$^2$

Sampling amount: 200 μL to 250 μL (HPLC Conditions)

HPLC system: LC-10AT system (from Shimadzu Corporation)

Detector: ultraviolet absorptiometer (wavelength: 290 nm)

Column: YMC Pack Pro C18, 4.6 mm I.D.×150 mm (from YMC Co., Ltd.)

Column temperature: 35° C.

Auto sampler temperature: 25° C.

Mobile phase:

A: water/acetonitrile/ammonium acetate (900:100:1, v/v/w)

B: water/acetonitrile/ammonium acetate (100:900:1, v/v/w)

A:B=600:400

The invention claimed is:

1. An acid addition salt of 3-(2-cyanophenyl)-5-(2-pyridyl)-1-phenyl-1,2-dihydropyridin-2-one, wherein the acid is selected from the group consisting of hydrochloric acid, hydrobromic acid, sulfuric acid, methanesulfonic acid and a hydrate of hydrochloric acid.

2. 3-(2-cyanophenyl)-5-(2-pyridyl)-1-phenyl-1,2-dihydropyridin-2-one hydrochloride.

3. 3-(2-cyanophenyl)-5-(2-pyridyl)-1-phenyl-1,2-dihydropyridin-2-one hydrobromate.

4. 3-(2-cyanophenyl)-5-(2-pyridyl)-1-phenyl-1,2-dihydropyridin-2-one sulfate.

5. 3-(2-cyanophenyl)-5-(2-pyridyl)-1-phenyl-1,2-dihydropyridin-2-one methanesulfonate.

* * * * *

UNITED STATES PATENT AND TRADEMARK OFFICE
CERTIFICATE OF CORRECTION

| | | |
|---|---|---|
| PATENT NO. | : 7,718,807 B2 | Page 1 of 1 |
| APPLICATION NO. | : 12/280403 | |
| DATED | : May 18, 2010 | |
| INVENTOR(S) | : Satoshi Nagato et al. | |

It is certified that error appears in the above-identified patent and that said Letters Patent is hereby corrected as shown below:

ON THE TITLE PAGE:

Please insert the following Related U.S. Application Data:

-- (60)      Related U.S. Application Data

Provisional application No. 60/879,012, filed on Jan. 8, 2007 --.

Signed and Sealed this

Thirtieth Day of November, 2010

David J. Kappos
*Director of the United States Patent and Trademark Office*